United States Patent
Loser

(10) Patent No.: US 6,386,758 B2
(45) Date of Patent: May 14, 2002

(54) METHOD FOR AUTOMATICALLY ALIGNING A MEDICAL INSTRUMENT IN THE BODY OF A PATIENT USING A COMPUTED TOMOGRAPHY APPARATUS

(75) Inventor: Michael Loser, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/778,452

(22) Filed: Feb. 7, 2001

(30) Foreign Application Priority Data

Feb. 9, 2000 (DE) .......................................... 100 05 628

(51) Int. Cl.⁷ ................................................ A61B 6/08
(52) U.S. Cl. ........................ 378/205; 378/162; 378/163
(58) Field of Search ................................. 378/205, 162, 378/163; 606/130

(56) References Cited

U.S. PATENT DOCUMENTS 5,575,798 A     11/1996    Koutrouvelis ............... 606/130

*Primary Examiner*—Robert H. Kim
*Assistant Examiner*—Irakli Kiknadze
(74) *Attorney, Agent, or Firm*—Schiff Hardin & Waite

(57) ABSTRACT

In a method for the automatic alignment of a medical instrument with respect to a target point in a patient body such as, for subsequent removal of a tissue sample or for therapy of a tumor in the target point, using a computed tomography apparatus with fluoroscopy mode, a guidance system aligns the medical instrument at a paracentesis point of the patient body in a CT image plane, and the spatial coordinates of the CT image plane are determined for the guidance system.

20 Claims, 3 Drawing Sheets

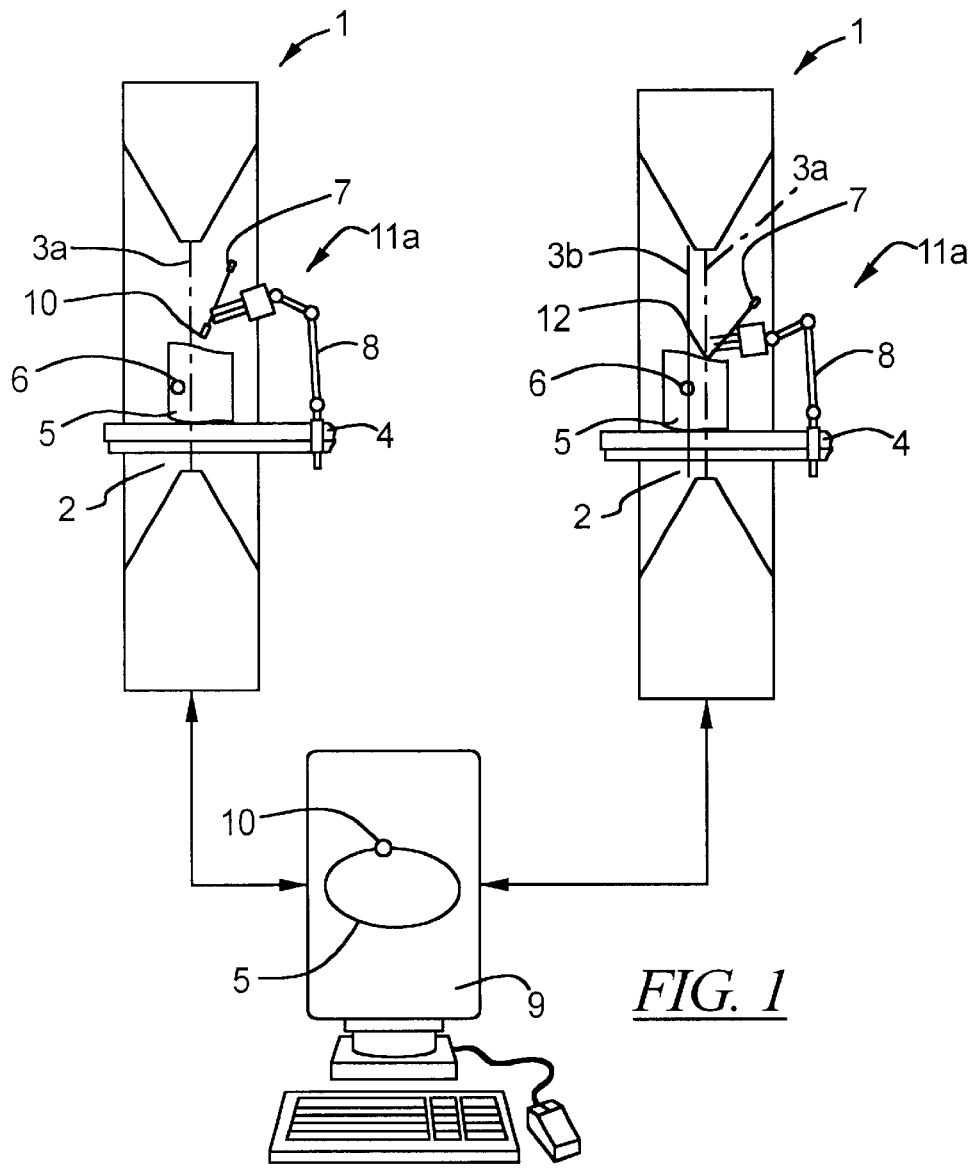
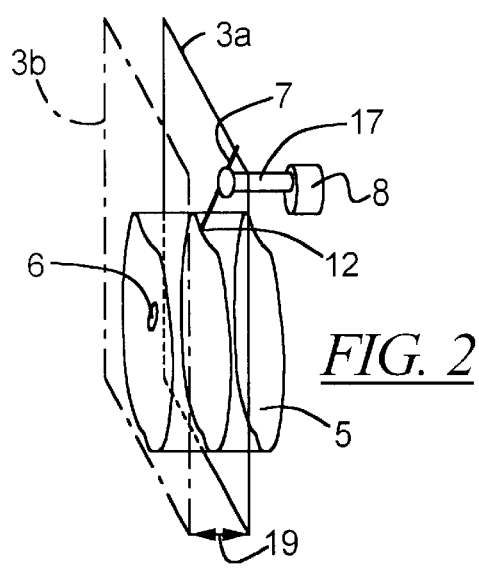
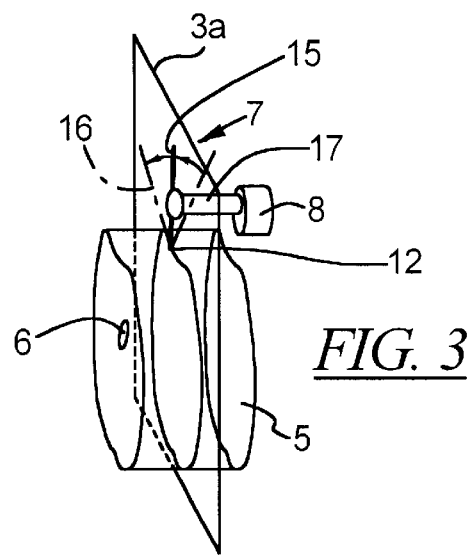
*FIG. 1*
*FIG. 2*
*FIG. 3*

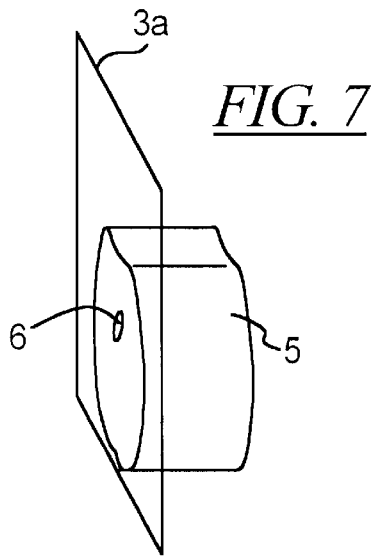
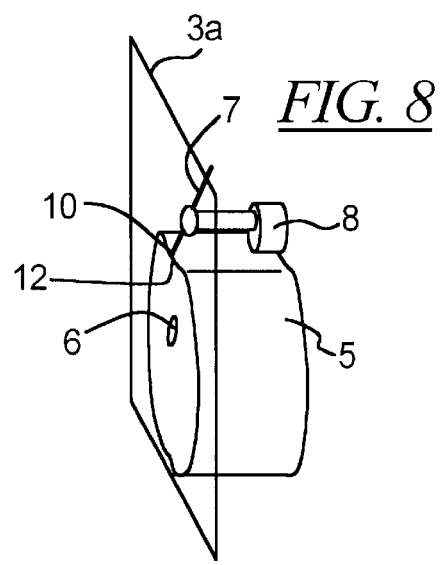
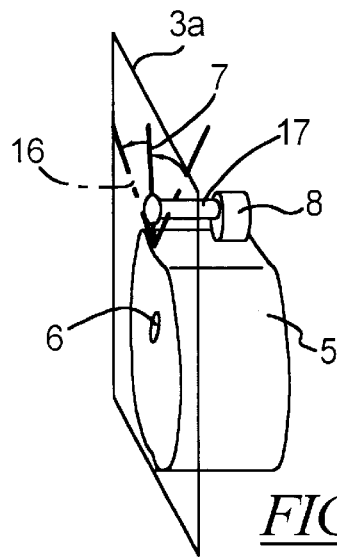
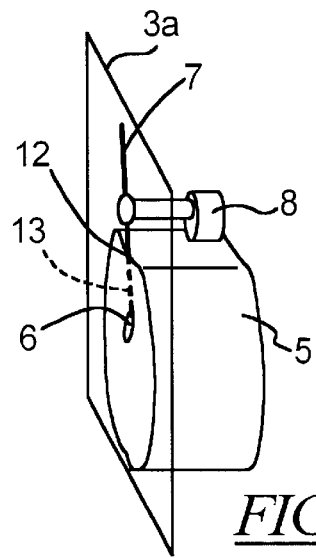
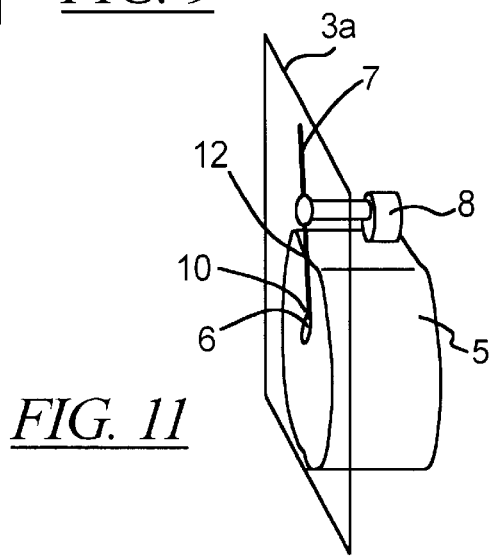

METHOD FOR AUTOMATICALLY ALIGNING A MEDICAL INSTRUMENT IN THE BODY OF A PATIENT USING A COMPUTED TOMOGRAPHY APPARATUS

BACKGROUND OF THE INVENTION

1. Field of the Invention

The present invention is directed to a method for the automatic alignment of a medical instrument with reference to a target point in the body of a patient, for example for subsequent removal of a tissue sample or for therapy of a tumor in the target point, using a computed tomography apparatus (with fluoroscopy mode).

2. Description of the Prior Art

A method for the alignment and introduction of a medical instrument to a target point in the body of a patient is known wherein the attending physician aligns a medical instrument at the paracentesis point of the body of the patient, perforates the skin and approaches the target point with imaging assistance using a computed tomography apparatus with fluoroscopy mode. The computed tomography apparatus with fluoroscopy mode thereby supplies image sequences of up to eight images/second (frames/second), so that the attending physician can observe the paracentesis motion directly at the picture screen.

In order to avoid direct exposure to X-rays, the attending physician grasps the medical instrument with forceps or tweezers, resulting in an indirect and impractical manipulation of the medical instrument.

SUMMARY OF THE INVENTION

An object of the present invention is to provide a method for alignment of a medical instrument with reference to a target point in the body of a patient that is automated and has an improved targeting precision.

The above object is achieved in accordance with the principles of the present invention in a method for automatically aligning a medical instrument relative to a target point in a patient's body, such as for subsequent removal of a tissue sample or for therapy of a tumor in the target point, using a computed tomography apparatus with fluoroscopy mode, wherein the paracentesis tip of a medical instrument is positioned at a paracentesis point of the patient's body using an automated guidance system, and wherein the medical instrument is positioned using the guidance system into a first position within a CT image plane that contains the paracentesis point. The spatial coordinates of the medical instrument at the first position are determined and stored. The medical instrument is then positioned by the automated guidance system into a second position within the CT image plane that differs from the first position. The spatial coordinates of the second position are determined and stored. The spatial coordinates of the CT image plane are then determined from the stored spatial coordinate for the first and second positions of the medical instrument.

Thus, the medical instrument in the inventive method is aligned with reference to a first CT image plane. As a result, the spatial coordinates of the first CT image plane are communicated to the guidance system of the medical instrument. The guidance system ("guide robot") that, for example, is motor-driven or pneumatically driven, can be attached to or in the proximity of the computed tomography apparatus without prior registration of its own spatial coordinates.

If, in the subsequent introduction of the instrument into the body of the patient, the paracentesis tip deviates from the previously defined, extended axis proceeding from the paracentesis point to the target point due to patient and/or organ movement, this can be automatically registered. The perforation procedure is then interrupted, corrected as needed, and then resumed.

Given a renewed perforation procedure, a correction angle can be taken into consideration in the guidance of the medical instrument, this correction angle, for example, being derived from the deviation of the extended axis, between the paracentesis location and the target point, and the initial, incorrect perforation channel of the medical instrument.

In an embodiment of the method, the paracentesis point at the patient body is located in the first CT image plane, whereas the target point in the patient body is located in a second CT image plane differing from the first plane.

In another embodiment of the method, both the paracentesis point at the patient body, as well as the target point in the patient body, are located in the first CT image plane

DESCRIPTION OF THE DRAWINGS

FIG. 1 is a schematic illustration of a guidance system with a medical instrument attached to a computed tomography apparatus for explaining a first embodiment of the inventive method.

FIGS. 2–5 are schematic illustrations of individual method steps of the first embodiment of the inventive method during alignment and/or introduction of the medical instrument.

FIGS. 7–11 are schematic illustrations of individual method steps of the second embodiment of the inventive method during alignment and/or introduction of the medical instrument.

DESCRIPTION OF THE PREFERRED EMBODIMENTS

Figure 4:
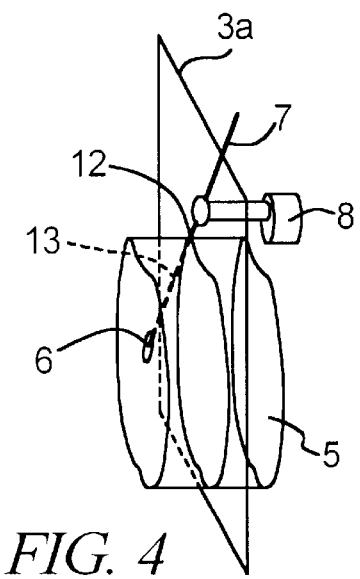

FIG. 1 shows a computed tomography apparatus 1 with the picture screen 9 of an appertaining EDP station. The medical instrument, a needle 7 here, is attached to the computed tomography apparatus 1, to the CT table 4 here, via a guidance system 8. The patient body 5 has been moved into the CT gantry 2 and has a paracentesis point 12 lying in a first CT image plane 3a. The position of the needle 7 is indicated at the picture screen 9. Dependent on whether the needle 7 is partially or completely located in the first CT image plane 3a, the paracentesis tip 10, a cross-section of the needle 7 or the entire length of the needle 7, can be observed at the picture screen 9.

In the guidance position 11a of the guidance system 8 connected to the EDP station (the guidance position 11a being shown in the upper left half of FIG. 1), the needle 7 is in the proximity of the paracentesis point 12 at the patient body 5.

The needle 7 is now adjusted such with the guidance system 8 so that, as shown in the upper right half of FIG. 1, in the guidance position 11b of the guidance system 8, the paracentesis tip 10 of the needle 7 is located at the paracentesis point 12 of the patient body 5 in the first CT image plane 3a. The illustration according to guidance position 11b of the guidance system 8 is schematically imaged on the picture screen 9 of the EDP station in FIG. 1. The picture screen 9 shows the patient body 5 with the paracentesis tip 10 of the needle 7 at the paracentesis point 12 in the first CT image plane 3a. The target point 6 is not visible at the picture screen 9 because it is located in a second CT image plane 3b. The second CT image plane 3d is spaced from the CT image plane 3a by a distance 19 (see FIG. 2).

Further details of the inventive method proceed from the illustrations of the following FIGS. 2–5.

FIG. 2 first shows the patient body 5 with the target point 6 in the second CT image plane 3b. The patient body 5 is arranged such inside the CT gantry 2 on the CT table 4 so that the paracentesis point 12 is in the first CT image plane 3a. The spatial coordinates of the target point 6 in the second CT image plane 3b are known from an examination previously implemented with the computed tomography apparatus 1.

The needle 7 is attached to (held by) the guidance system 8. In a first method step, the paracentesis tip 10 of the needle 7 is located at the paracentesis point 12 of the patient body 5. This can occur automatically by placing a marker, for example, a metallic marker (not shown), to which the guidance system 8 can align itself in a known way, at the paracentesis point 12 of the patient body 5.

As shown in FIG. 2, the needle 7 as a whole is not yet situated in the first CT image plane 3a, and the guidance system 8 also does not yet have the information about the spatial coordinates of the first CT image plane 3a, since the guidance system 8 is attached to or in the proximity of the computed tomography apparatus 1 without previous spatial coordinate balancing.

As show in FIG. 3, the needle 7 is positioned in a first position 15 in the first CT image plane 3a. The term "positioning" is used herein as meaning any type of movement of the needle 7, i.e. any and all types of turning, displacement or other movement.

As a result of storing the dimensional data, particularly the length, of the needle 7 in the EDP station, a determination can be made when the needle 7 is completely situated in the first CT image plane 3a after being positioned in the first position 15. This is the case when the entire length of the needle 7 becomes imaged on the picture screen 9, which can be automatically detected (for example, by counting the number of pixels).

As soon as the needle 7 is completely located in the first CT image plane 3a, the spatial coordinates of the needle 7 are stored and communicated to a memory of the EDP station of the guidance system 8. In order to be able to completely inform the guidance system 8 of the position of the first CT image plane 3a, the needle 7 is now positioned in a second position 16—which deviates from the first position 15—in the first CT image plane 3a, whereupon the spatial coordinates of the needle 7 are determined anew. When the guidance axis 17 of the guidance system 8 resides at a right angle to the first CT image plane 3c, the second position 16 can, for example, be achieved by rotation around the guidance axis 17 of the guidance system 8.

By relating the spatial coordinates of the needle 7 determined at the respective positions described above, the spatial coordinates of the first CT image plane 3a can be determined and communicated to the guidance system 8, since the position of a plane can be unambiguously defined by the spatial coordinates of two intersecting straight lines in the plane.

Subsequently, the needle 7 is automatically aligned over the known spatial coordinates of the target point 6 so that the projected extension of the needle 7, namely the axis 13, passes through the target point 6 (FIG. 4).

Figure 5:
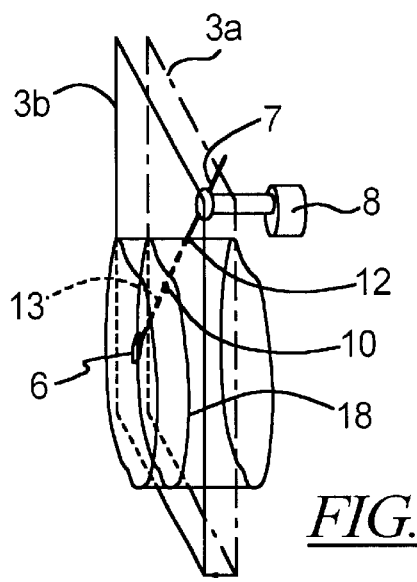

Subsequently, the guidance system 8 inserts the needle 7 into the patient body 5 linearly along the extended axis 13, and the needle 7 moves toward the target point 6 in the second CT image plane 3b until the target point 6 is reached. FIG. 5 shows the paracentesis tip 10 in an intermediate CT image plane 18 during the introduction that is located between the first CT image plane 3a, which contains the paracentesis point 12, and the second CT image plane 3b, which contains the target point 6.

All method steps from the positioning of the paracentesis tip 10 of the needle 7 at the paracentesis point 12 of the patient body 5 by the alignment and introduction of the needle 7, to the final attainment of the target point 6, can sequence fully automatically.

A particular advantage of the inventive method is that the guidance system 8 can be attached to the computed tomography apparatus 1 at a practically arbitrary location and the spatial coordinates of the first CT image plane 3a are automatically determined during the executive sequence of the inventive method, so that, finally, the needle 7 is aligned at the paracentesis point 12, is inserted and can be guided to the target point 6.

If, upon insertion of the needle 7, i.e. on the path between the paracentesis point 12 and the target point 6, a deviation of the paracentesis path of the needle 7 from the designated path of the axis 13 occurs (for example, due to patient and/or organ movement), this is detected by an ongoing acquisition of the spatial coordinates of the paracentesis tip 10 of the needle 7, and the paracentesis event can be interrupted and corrected or repeated from the start with a new alignment of the needle 7. The deviation angle that occurs between the paracentesis tip 10 of the needle 7, the paracentesis point 12 at the patient body 5, and the axis 13 can be automatically acquired and taken into consideration for corrective use given a renewed paracentesis procedure.

Figure 6:
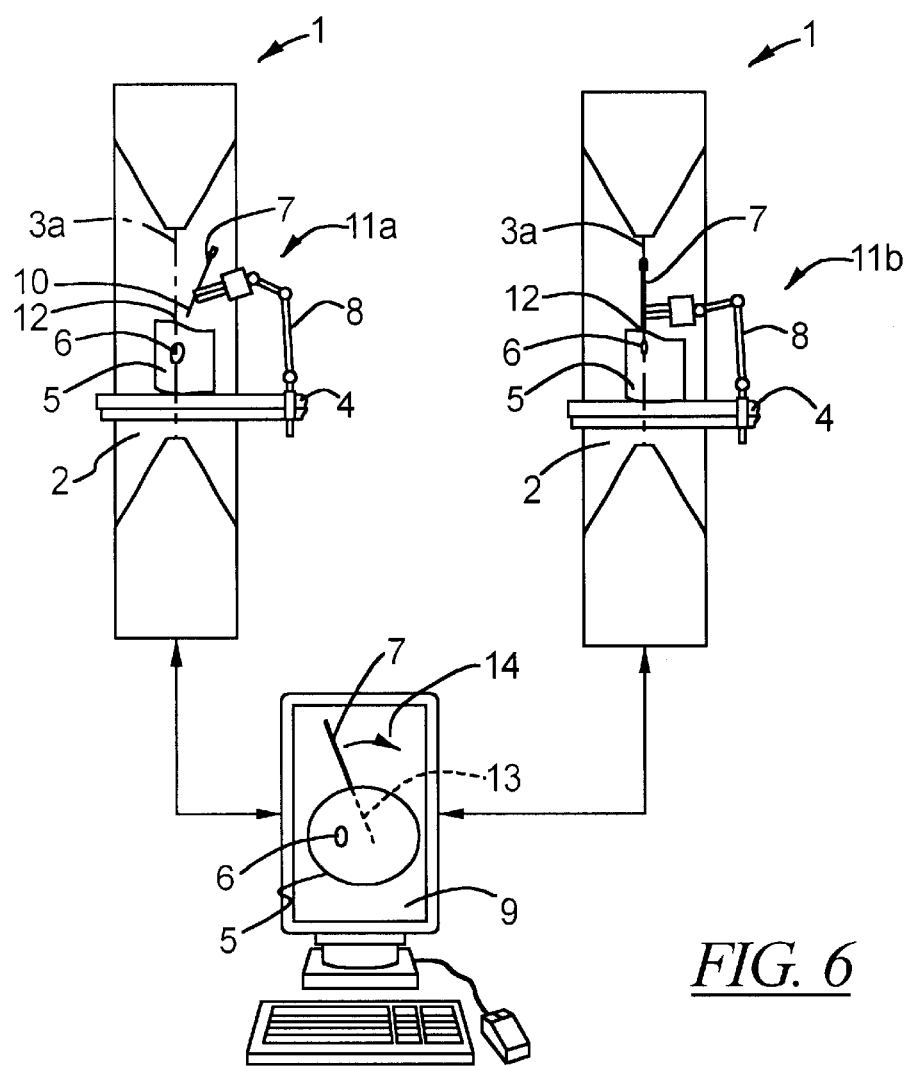
FIG. 6 is a schematic illustration of a guidance system with a medical instrument attached to a computed tomography apparatus for explaining a second version of the inventive method.

Analogously to FIG. 1, FIG. 6 shows the initial situation of a second embodiment of the method, again employing a computed tomography apparatus 1 with the picture screen 9 of an appertaining EDP station. The medical instrument— the needle 7 here—is attached to the computed tomography apparatus 1, to the CT table 4 here, via a guidance system 8. The patient body 5 has been moved into the CT gantry 2 and has a target point 6 in the first CT image plane 3a.

The position of the needle 7 is displayed at the picture screen 9. Dependent on whether the needle 7 is partially or completed situated in the first CT image plane 3a, the paracentesis tip 10, a cross-section of the needle 7, or the entire length of the needle 7 can be observed at the picture screen 9.

In the guidance position 11a of the guidance system 8 that is also connected to the EDP station and that is shown in the upper left half of FIG. 6, the needle 7 is located in the proximity of the paracentesis point 12 at the patient body 5. The paracentesis point 12 is located in the CT image plane 3a.

The needle 7 is now adjusted with the guidance system 7 so that, as shown in the upper right half of FIG. 6 in the guidance position 11b of the guidance system 8, the needle 7 with the paracentesis tip 10 at the paracentesis point 12 of the patient body 5 is completely located in the CT image plane 3a. The illustration according to guidance position 11b of the guidance system 8 is schematically shown on the picture screen 9 of the EDP station in FIG. 6.

The goal is to position the needle 7, extended by the axis 13, on the picture screen 9 within the first CT image plane 3a such that, for example by rotation in the direction 14, it can be aligned such that the extended axis 13 intersects the target point 6, whose spatial coordinates are known. This can ensue automatically. When this has been accomplished, the needle 7 can be linearly introduced along the axis 13 until the target point 6 is reached.

Further details of the second version of the inventive method proceed from the illustrations of the following FIGS. 7–11.

FIG. 7, first, shows the patient body 5 with the target point 6, which represents a specific organ or a tumor to be removed. The patient body 5 is arranged within the CT gantry 2 on the CT table 4 so that the target point 6 is located in the first CT image plane 3a. The spatial coordinates of the target point 6 are known.

The guidance system 8, which is not shown in FIG. 7 and to which the needle 7 is attached, is shown in FIG. 8. In a first method step, the paracentesis tip 10 of the needle 7 is located at the paracentesis point 12 of the patient body 5. This can occur automatically by placing a marker for example, a metallic marker (not shown), to which the guidance system 8 can align itself in a known way, at the paracentesis point 12 of the patient body 5.

As shown in FIG. 8, the needle 7 is not yet located in the first CT image plane 3a, and the guidance system 8 does not yet have the information about the spatial coordinates of the first CT image plane 3a, since the guidance system 8 is attached to or in the proximity of the computed tomography apparatus 1 without previous spatial coordinate referencing.

As shown in FIG. 9, the needle 7 is then positioned in a first position 15 in the CT image plane 3a. Again, the term "positioning" is used herein as meaning any type of movement of the needle 7, i.e. any and all types of turning, displacement or other movement.

As a result of storing the dimensional data, particularly the length, of the needle 7 in the EDP station, a determination can be made when the needle 7 is completely situated in the first CT image plane 3a after being positioned in the first position 15. This is the case when the entire length of the needle 7 becomes imaged on the picture screen 9, which can be automatically detected (for example, by counting the number of pixels).

As soon as the needle 7 is completely located in the first CT image plane 3a, the spatial coordinates of the needle 7 are stored and communicated to a memory of the EDP station of the guidance system 8. In order to be able to completely inform the guidance system 8 of the position of the first CT image plane 3a, the needle 7 is now positioned in a second position 16—which deviates from the first position 15—in the first CT image plane 3a, whereupon the spatial coordinates of the needle 7 are determined anew. When the guidance axis 17 of the guidance system 8 resides at a right angle to the first CT image plane 3a, the second position 16 can, for example, be achieved by rotating around the guidance axis 17 of the guidance system 8.

By relating the spatial coordinates of the needle 7 determined as just described, the spatial coordinates of the first CT image plane 3a can be determined and communicated to the guidance system 8, since the position of a plane can be unambiguously defined by the spatial coordinates of two intersecting straight lines in the plane. With this spatial coordinate information, the guidance system 8 can displace or rotate the needle 7 within the CT image plane 3 without leaving the CT image plane 3.

After the needle 7, for example as a result of rotation in the direction 14 which is seen on the picture screen 9 according to FIG. 6, is aligned such within the first CT image plane 3a that the extension of the needle 7, namely the axis 13, passes through the target point 7, the stage of the method shown in FIG. 10 has been reached.

Subsequently, the guidance system 8 linearly inserts the needle 7 into the patient body 5 along the extended axis 13 and moves it within the CT image plane 3a toward the target point 6 until the target point 6 is reached (FIG. 11). The subject located at the target point 6, for example the tissue thereat or the tumor thereat, can now be treated.

All method steps from the positioning of the paracentesis tip 10 of the needle 7 at the paracentesis point 12 of the patient body 5 by the alignment and introduction of the needle 7, to the final attainment of the target point 6, can sequence fully automatically.

A particular advantage of the inventive method is that the guidance system 8 can be attached to the computed tomography apparatus 1 at a practically arbitrary location and the spatial coordinates of the first CT image plane 3a are automatically determined during the executive sequence of the inventive method, so that the needle 7 is aligned at the paracentesis point 12, is inserted, and can be guided to the target point 6.

If, upon insertion of the needle 7, i.e. on the path between the paracentesis point 12 and the target point 6, a deviation of the paracentesis path of the needle 7 from the designated path of the axis 13 occurs (for example, due to patient and/or organ movement), this is detected by an ongoing acquisition of the spatial coordinates of the paracentesis tip 10 of the needle 7, and the paracentesis event can be interrupted and corrected or repeated from the start with a new alignment of the needle 7. The deviation angle that occurs between the paracentesis tip 10 of the needle 7, the paracentesis point 12 at the patient body 5, and the axis 13 can be automatically acquired and taken into consideration for corrective use given a renewed paracentesis procedure.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for automatically aligning a medical instrument relative to a target point in a patient's body using a computed tomography apparatus with fluoroscopy mode, comprising the steps of:

(a) positioning a paracentesis tip of the medical instrument at a paracentesis point of the patient's body using an automated guidance system;

(b) using said automated guidance system, positioning the medical instrument in a first position in a CT image plane that contains the paracentesis point;

(c) determining and storing spatial coordinates of the medical instrument in said first position;

(d) using said automated guidance system, positioning the medical instrument in a second position in said CT image plane that differs from said first position;

(e) determining and storing spatial coordinates of the medical instrument in said second position; and (f) determining spatial coordinates of said CT image plane from the spatial coordinates determined and stored in steps (c) and (e).

2. A method as claimed in claim 1 comprising employing a paracentesis needle as said medical instrument.

3. A method as claimed in claim 1 comprising storing dimensional data of said medical instrument and positioning said medical instrument, in steps (b) and (d), by identifying and acquiring dimensions of said medical instrument in said CT image plane and comparing said dimensions to the stored dimensional data.

4. A method as claimed in claim 1 wherein said automated guidance system has a guidance axis, and wherein step (d) comprises positioning the medical instrument in said second position by rotating said medical instrument around said guidance axis from said first position to said second position.

5. A method as claimed in claim 1 wherein said CT image plane is a first CT image plane, and wherein said target point is disposed in a second CT image plane spaced from said first CT image plane, and comprising the additional step of rotating said medical instrument out of said first CT image plane until an extended projection axis of said medical instrument intersects said target point in said second CT image plane.

6. A method as claimed in claim 5 comprising storing spatial coordinates of said axis.

7. A method as claimed in claim 5 comprising introducing said medical instrument into the patient's body along said axis until said paracentesis tip reaches said target point in said second CT image plane.

8. A method as claimed in claim 7 comprising continually acquiring spatial coordinates of said paracentesis tip of said medical instrument while said medical instrument is being introduced into the patient's body, and storing said coordinates of said paracentesis tip.

9. A method as claimed in claim 8 comprising continually comparing the stored spatial coordinates of the axis of the medical instrument and the stored spatial coordinates of the paracentesis tip while said medical instrument is introduced into the patient's body.

10. A method as claimed in claim 9 comprising, if the spatial coordinates of the paracentesis tip deviate from the spatial coordinates of the axis during introduction of the medical instrument into the patient's body, interrupting introduction of the medical instrument into the patient's body.

11. A method as claimed in claim 9 comprising, after interrupting introduction of the medical instrument into the patient's body, renewing introduction of the medical instrument into the patient's body along a corrected path.

12. A method as claimed in claim 11 comprising, in the renewed introduction, determining said corrected path using a correction angle based on the deviation of the spatial coordinates of the axis and the spatial coordinates of the paracentesis tip.

13. A method as claimed in claim 1 comprising rotating said medical instrument within said CT image plane until a projected extended axis of said medical instrument intersects said target point in said CT image plane.

14. A method as claimed in claim 13 comprising determining and storing spatial coordinates of said axis.

15. A method as claimed in claim 14 comprising introducing the medical instrument into the patient's body until the paracentesis tip of the medical instrument reaches the target point in the CT image plane.

16. A method as claimed in claim 15 comprising continually acquiring spatial coordinates of said paracentesis tip of said medical instrument while said medical instrument is being introduced into the patient's body, and storing said coordinates of said paracentesis tip.

17. A method as claimed in claim 16 comprising continually comparing the stored spatial coordinates of the axis of the medical instrument and the stored spatial coordinates of the paracentesis tip while said medical instrument is introduced into the patient's body.

18. A method as claimed in claim 17 comprising, if the spatial coordinates of the paracentesis tip deviate from the spatial coordinates of the axis during introduction of the medical instrument into the patient's body, interrupting introduction of the medical instrument into the patient's body.

19. A method as claimed in claim 18 comprising, after interrupting introduction of the medical instrument into the patient's body, renewing introduction of the medical instrument into the patient's body along a corrected path.

20. A method as claimed in claim 19 comprising, in the renewed introduction, determining said corrected path using a correction angle based on the deviation of the spatial coordinates of the axis and the spatial coordinates of the paracentesis tip.

* * * * *